United States Patent [19]

Shibanai et al.

[11] Patent Number: 4,728,510

[45] Date of Patent: Mar. 1, 1988

[54] BATH PREPARATIONS AND METHOD FOR PRODUCING THE SAME

[75] Inventors: Ichiro Shibanai, Tokyo; Kenji Nakamura, Osaka, both of Japan

[73] Assignee: Japan Liquid Crystal Co., Ltd., Tokyo, Japan

[21] Appl. No.: 832,745

[22] Filed: Feb. 24, 1986

[30] Foreign Application Priority Data

Jun. 13, 1985 [JP] Japan .................. 60-129444

[51] Int. Cl.$^4$ .................. A61K 37/52; A61K 35/12; A61K 31/715; C08B 30/18

[52] U.S. Cl. .................. 424/94.5; 424/95; 514/58; 514/251; 514/458; 514/478; 536/46; 428/402.2

[58] Field of Search .................. 424/94, 95, 94.5; 514/58; 536/46; 428/402.2

[56] References Cited

U.S. PATENT DOCUMENTS

4,352,794 10/1982 Koch .................. 514/58

FOREIGN PATENT DOCUMENTS

2092890 8/1982 United Kingdom .................. 514/58

OTHER PUBLICATIONS

J. Szejtl:, Cyclodextrins pp. 78 and 79, 1981, Ashland.

Chem. Abst. 104: 39526s 1986.
Chem. Abst 104: 10409u, 1986.
Chem Abst. 102: 202916p 1985.
Chem. Abst. 83: 120672f, 1975.
Chem. Abst. 83 152403k, 1975.

*Primary Examiner*—J. R. Brown
*Assistant Examiner*—John W. Rollins, Jr.
*Attorney, Agent, or Firm*—Burgess, Ryan & Wayne

[57] ABSTRACT

A bath preparations comprise a cyclodextrin clathrate compound of a component of milk. The bath preparations may further comprise egg white and/or at least one vitamin selected from the goup consisting of vitamin A, vitamins B, vitamin C, Vitamin D, vitamin E, vitamin F and vitamin P. The bath preparations may be used together with a saccharifying enzyme, which is mixed with the bath preparations or which is insulated from the bath preparations.

A method for producing the bath preparations comprises contacting milk, which is selected from the group consisting of cow's milk, components of cow's milk, powdered milk, evaporated milk, components of evaporated milk, raw cream and components of raw cream, with cyclodextrin to form a cyclodextrin clathrate compound of the component of milk, and mixing the cyclodextrin clathrate compound of the component of milk with other raw materials of baths.

21 Claims, No Drawings

BATH PREPARATIONS AND METHOD FOR PRODUCING THE SAME

TECHNICAL FIELD OF THE INVENTION

The present invention relates to bath preparations, especially bath preparations utilizing cyclodextrin clathrate compound. The present invention also relates to a method for producing the bath preparations.

PRIOR ART

It has been said from the ancient times that a milk bath is good for beauty. In fact, active principles in milk have effects for refreshing the skin. However, practically, milk is scarcely used in bath preparations.

The reason why milk is not used in bath preparations is because it is raw and perishable, because it is difficult to administer the industrial production of bath preparations from milk, and because milk has a characteristic odor, which somebody likes while somebody dislikes.

OBJECT OF THE INVENTION

An object of the present invention is to change a component of milk, such as cow's milk, to a material, which is stable, and to use such a material in bath preparations so as to enhance the effects for refreshing the skin.

SUMMARY OF THE INVENTION

The bath preparations of the present invention are characterized in that they comprise a cyclodextrin clathrate compound of a component of milk. The bath preparations of the present invention may comprise other raw materials of baths, which have been conventionally used as baths, in addition to the cyclodextrin clathrate compound of a component of milk. It is preferred that the bath preparations of the present invention further comprise at least one vitamin.

The method for producing bath preparations of the present invention is characterized by contacting milk with cyclodextrin to form a cyclodextrin clathrate compound of a component of the milk, and mixing the cyclodextrin clathrate compound of the component of milk with other raw materials of baths.

DETAILED DESCRIPTION OF THE INVENTION

The milk, which is used in the present invention and a component of which is entrapped in a cyclodextrin to form a cyclodextrin clathrate compound of a component of milk, may be cow's milk, components of cow's milk, powdered milk, evaporated milk, components of evaporated milk, raw cream, components of raw cream, or the like.

The cyclodextrin of the present invention may be alpha-cyclodextrin, beta-cyclodextrin, gamma-cyclodextrin, a derivative of cyclodextrin, or a mixture thereof. The cyclodextrin may be a powder or a cyclodextrin-containing starch decomposition product (for example, Celdex CH-20, manufactured by Nippon Shokuhin Kako K.K.)

The cyclodextrin clathrate compound of a component of milk, wherein the component of milk is entrapped in cyclodextrin, may be produced by way of a saturated aqueous solution method or a kneading method.

More specifically, in the saturated aqueous solution method, a predetermined amount of milk is added to a saturated aqueous solution of cyclodextrin or a supersaturated aqueous solution of cyclodextrin, and then, the solution is agitated for a time between tens of minutes and some hours, and a cyclodextrin clathrate compound is obtained.

In the kneading method, water or hot water is added to cyclodextrin to form a slurry, and then, a required amount of a component of milk is added to the slurry. Thereafter, the slurry is agitated well in a kneader for a time between tens of minutes and some hours, and a pasty material containing a cyclodextrin clathrate compound is obtained. If powder cyclodextrin is used in this kneading method, hot water, the weight of which is between 0.1 and 6 times the weight of the cyclodextrin, is added to the cyclodextrin to form a paste or suspension.

When a cyclodextrin-containing starch decomposition product or a cyclodextrin containing malt syrup available on the market is used, about the same weight of water as that of decomposition product or syrup is added or no water is added, since the decomposition product or syrup contains some water between about 25 to 40% or 70 to 80%.

The paste produced by the above-described saturated aqueous solution method or kneading method and containing the cyclodextrin clathrate compound is rinsed, and then is dried by spraying, ventilating or freezing method and a powder clathrate compound is obtained.

The ratio of the component of milk, which is used as a guest, and the cyclodextrin, which is used as a host, is not limited as long as the component of milk can be included in the cyclodextrin. For example, molar ratio of about 1:1 can be used.

For example, 20 parts by weight of components of milk, 80 parts by weight of Celdex CH-20 (manufactured by Nippon Shokuhin Kako K.K., malt syrup of cyclodextrin) and water (between 80 and 160 parts by weight) were mixed at a temperature below 70° C., and were agitated for several hours. The clathrate compound thus obtained was rinsed and then was dried by spray drying or vacuum drying to produce clathrate composition in a powder form.

When a commercially available cyclodextrin containing malt syrup is used to produce a cyclodextrin clathrate composition of a component of milk, scorching, i.e., oxidation, of the syrup may occur if the treating temperature is high. As a result, there may occur a problem that a component of milk cannot be fully included in the cyclodextrin. Further, there may occur a problem that a cyclodextrin clathrate compound cannot be dissociated, i.e., ring opening does not occur, until the temperature reaches a relatively high temperature, when a commercially available cyclodextrin containing malt syrup is used to produce a cyclodextrin clathrate compound of a component of milk.

In such a case, it is preferred that the end-groups of the maltooligosaccharide syrup are almost completely reduced, and that reduced cyclodextrin syrup, which is a mixture of the reduced syrup and cyclodextrin, is used to include a component of milk with cyclodextrin to form a cyclodextrin clathrate compound of a component of milk. The milk is selected from the group consisting of cow's milk, components of cow's milk, powdered milk, evaporated milk, components of evaporated milk, raw cream and components of raw cream.

The above-described reduced cyclodextrin syrup, i.e., the reduced syrup containing cyclodextrin, of the present invention is produced in a manner set forth below.

First, reducing end-groups of maltooligosaccharide syrup are almost completely reduced to produce reduced syrup. For example, maltooligosaccharide mixture, such as glucose, maltose or maltoriose, obtained by hydrolyzing starch with acid or enzyme, is hydrogenated under nickel catalyst and high pressure. In this case, it is preferred that the amount (or pressure) of hydrogen is set, for example, between 100 and 200 Kg/cm$^2$, and that the reaction is carried out at a temperature between about 70° and 160° C.

As a result, the reducing end-groups of maltooligosaccharide syrup are hydrogenated and are changed to the sugaralcohol corresponding thereto, and their reducing capability is lost. More specifically, glucose, maltose and maltoriose are changed to sorbitol, maltitol and maltotriitol, respectively, and their reducing capability is lost.

The sugar concentration of malt syrup is usually between 30 and 70%, however, Dextrose Equivalent, D.E., i.e., the ratio of reducible sugar to all the solid content, becomes zero after hydrogenation.

Since the reducing end-groups are lost after hydrogenation, oxidation will not occur readily. Accordingly, the stability against high temperature is increased. Further, the syrup will not be easily colored, since the reaction with amino groups, such as amino acid, i.e., amino carbonyl reaction, does not occur.

The mixture of the above-described reduced malt syrup and cyclodextrin can be used as the reduced cyclodextrin syrup which is used in the method of the present invention.

Preferably, malt syrup containing cyclodextrin, for example Celdex CH-20 or Celdex CH-30, manufactured by Nippon Sohkuhin Kako K.K., is hydrogenated in a foregoing manner to produce the reduced cyclodextrin syrup.

In this case, since the cyclodextrin is not reducible and since the Dextrose Equivalent value thereof, (D.E., i.e., the ratio of reducible sugar to all the solid content) is zero, the cyclodextrin is not affected during the hydrogenation process and remains as it is. Contrary to this, the reducing end-groups of maltooligosaccharide syrup, containing glucose, maltose or the like except for cyclodextrin, are hydrogenated and are changed to a sugaralcohol corresponding thereto.

Furthermore, pure alpha-cyclodextrin, beta-cyclodextrin, gamma-cyclodextrin, the derivative of cyclodextrin, or the mixture thereof may be added to the reduced cyclodextrin syrup thus obtained.

Alternatively, after pure malt syrup is reduced, cyclodextrin may be added to the reduced malt syrup to form the reduced cyclodextrin syrup.

Then, utilizing the thus obtained reduced cyclodextrin syrup, the component of milk similar to those described above is included in the cyclodextrin by way of a saturated aqueous solution method or a kneading method similar to those described above, and the cyclodextrin clathrate compound of a component of milk, which has been described above, is produced.

Thereafter, the cyclodextrin clathrate compound of a component of milk, which was obtained by including the component of milk in the powder form cyclodextrin clathrate compound, the cyclodextrin-containing syrup, i.e., starch decomposition product, or the reduced cyclodextrin syrup, is stirred well with other raw materials of baths, such as, water softener, materials performing bleaching effect or sterilizing effect, or materials applied to medical purpose, perfume, coloring matter, and so on, in a kneader. As described above, bath preparations of a powder form of the present invention may be obtained.

Alternatively, the mixture, comprising the cyclodextrin clathrate compound of milk and the other raw material of baths and stirred in the kneader, may be pressed to form blocks, and the blocks may be crushed and sieved to form granular bath preparations of the present invention.

Further alternatively, the above-mentioned mixture stirred in the kneader may be subjected to compression mold by means of a tablet machine to form bath preparations of a tablet type of the present invention.

According to the present invention, the following materials may be used as the conventionally known raw materials of baths together with the cyclodextrin clathrate compound of a component of milk.

(A) Inorganic salts:

Sodium chloride, sodium hydrogencarbonate, sodium carbonate, borax, sodium sulfate, sodium sulfide, sodium sesquicarbonate, sodium nitrate, sodium thiosulfate, polyphosphoric acid sodium, sodium phosphate, calcium thiosulfate, calcium oxide, calcium nitrate, calcium carbonate, calcium hydrogenphosphate, potassium sulfide, potassium nitrate, potassium bromide, potassium chloride, aluminum sulfate, magnesium carbonate, heavy magnesium carbonate, ammonium chloride, iron sulfate, and so.

(B) Inorganic acids:

Boric acid, metasilicic acid, silicic acid anhydride, and so on.

(C) Organic acids:

Benzoic acid, citric acid, fumaric acid, tartaric acid, pyrrolidonecarboxylic acid, and so on.

(D) Medicinal herbs:

*Foeniculi fructus*, extracts of *Phellodendri cortex*, Japanese Valerian, Camomile, *Scutellariae radix*, *Cinnamomum cortex*, *Carthami flos*, *Nulpharis rhizoma*, Saffron, *Paeoniae radix*, *Houttuyniae herba*, *Zingiberis recens rhizoma*, *Acorus calamus*, *Cnidii rhizoma*, *Atractylodis lancea rhizoma*, *Aurantii nobbis percarpium*, *Angelicae radix*, Bitter Orange Peel, *Ginseng radix*, *Menthae folium*, *Angelicae dahuricae radix*, *Atractylodis rhizoma*, *Eriobotyrae forium*, Hoelen, Borneol, and so on.

(E) Oils:

Olive oil, soybean oil, bran oil, extracts of rice barn oil, liquid paraffin, vaseline, and so on.

(F) Perfumes:

(i) Natural perfumes;

Lavender, jasmin, lemon, rose, orange, pine, and so on.

(ii) Synthetic perfumes;

Geraniol, citronellol, phenylethyl alcohol, benzyl acetate, and so on.

(G) Coloring matters:

Amaranth, Tartrazine, Fast Green FCF, Brilliant Blue FCF, Rhodamine B, Orange II, Uranine, Alizarine Cyanine Green F, Indigo, chlorophyll, riboflavin, annato, crocin, cochineal, safflower, anthraquinone, and so on.

(F) Alcohols:

Ethanol, stearyl alcohol, isopropyl alcohol, cetyl alcohol, hexadecyl alcohol, and so on.

(G) Polyols:

Glycerol, propylene glycol, sorbitol, and so on.

(H) Others:

Sulfur, mineral powder, incrustation of hot-spring water, neutral china clay, sodium salicylate, sodium carboxymethylcellulose, powder of yolk, roasted rice bran, powder of mica, polyvinyl pyrolidone, and so on.

The above-described raw materials of baths may be a powder type, a granular type, a tablet type, a crystal type, or a pasty type, and the medicinal herbs may retain their shapes or may be crushed.

It is preferred to add egg white or vitamins in order to enhance effects for refreshing the skin.

When egg white is added, upon contacting a component of milk with cyclodextrin to form a cyclodextrin clathrate compound of a component of milk, the egg white is mixed with cyclodextrin or the reduced cyclodextrin syrup together with the component of milk. Thereafter, the cyclodextrin clathrate compound of a component of milk is dried to form a powder type cyclodextrin clathrate compound. The thus obtained powder type cyclodextrin clathrate compound of a component of milk is mixed with other raw materials of baths.

As vitamins used in the present invention, vitamin A, vitamins B, vitamin C, Vitamin D, vitamin E, vitamin F or vitamin P is suitable. The vitamins, as well as a component of milk, may be mixed with cyclodextrin-containing aqueous solution, cyclodextrin-containing slurry or the reduced cyclodextrin syrup together with the component of milk when the component of milk is included in the cyclodextrin to form a cyclodextrin clathrate compound of a component of milk. Especially, in case of oil-soluble vitamins, such as vitamin A, D or E, after the component of milk is included by the reduced cyclodextrin or the like, the vitamins are added to the liquid material containing the cyclodextrin clathrate compound of the component of milk, prior to drying cyclodextrin clathrate compound. Thereafter, the cyclodextrin clathrate compound is dried at a relatively low temperature to form a powder while the destruction of the vitamins is prevented.

It is preferred that oil soluble vitamins are emulsified prior to addition to the liquid containing cyclodextrin clathrate compound, since they are easily deteriorated. In this case, it is also preferred that the emulsifying operation is carried out by utilizing the cyclodextrin clathrate compound as a surface active agent. For example, vitamin oil and water, the amounts of which are almost the same by molar ratio, are prepared, and a thickening agent, such as sodium alginate, and a small amount of cyclodextrin clathrate compound are added thereto so as to be emulsified.

Furthermore, vitamins per se may be contacted with cyclodextrin or the reduced cyclodextrin syrup to form cyclodextrin clathrate compound of a powder type, and they may be finally mixed with other raw materials of the baths together with cyclodextrin clathrate compound of a component of milk.

In order to increase antiseptic effects or fungicidal effects, it is preferred that about 1% of glycine and alcohol, respectively, which are emulsified by cyclodextrin, are added to a liquid containing cyclodextrin clathrate compound of a component of milk and are powdered together with the cyclodextrin clathrate compound of the component of milk.

Furthermore, perfume may be included in cyclodextrin or the reduced cyclodextrin syrup to form a cyclodextrin clathrate compound powder, and it may be finally mixed with other raw materials of the baths together with powder cyclodextrin clathrate compound of a component of milk. Alternatively, a small amount of cyclodextrin is mixed with the perfume to emulsify it, and the emulsion is added to liquid containing cyclodextrin clathrate compound of a component of milk, and it is powdered together with the cyclodextrin clathrate compound of the component of milk. The perfume used in the present invention is not limited, and it is preferred that flavor of milk is used in order to increase the atmosphere of a milk bath in conjunction with the component of milk included in the cyclodextrin clathrate compound.

Generally speaking, the cyclodextrin clathrate compound obtained from powder cyclodextrin or cyclodextrin syrup is difficult to be dissociated, in other words, opening of rings does not occur easily, and the cyclodextrin clathrate compound under the dry conditions is not dissociated until the temperature reaches about between 80° and 130° C. Accordingly, when the bath preparations, wherein such cyclodextrin clathrate compound is contained, are used, it is preferred that the bath preparations are dissolved in hot water.

As described above, the bath preparations of the present invention may be previously dissolved in hot water and are poured in the bath. However, it is preferred that the rings of the cyclodextrin clathrate compound are dissociated at a temperature of usual bath and that the component of milk included in the cyclodextrin clathrate compound is dissolved.

The cyclodextrin clathrate compound produced from the reduced cyclodextrin syrup may be easily dissociated, i.e., opening of its rings may be easily occur. However, it is preferred that such a cyclodextrin clathrate compound is further easily dissociated.

For such a purpose, it is preferred that a very small amount of saccharifying enzyme is used with the bath preparations of the present invention. Alph-amylase, or Cyclomaltodextrin glucanotransferase, for example, may be used as the saccharifying enzyme. In this case, after the component of milk is included in the cyclodextrin and is dried to form powder, it may be mixed with the saccharifying enzyme together with other materials of the baths. Alternatively, it may be insulated from the saccharifying enzyme so that the saccharifying enzyme does not contact the cyclodextrin clathrate compound, and the saccharifying enzyme and the cyclodextrin clathrate compound may be poured together into a bath. Examples of methods for insulating the saccharifying enzyme from the cyclodextrin clathrate compound are as follows.

EXAMPLE 1

The cyclodextrin clathrate compound and the saccharifying enzyme are kept in separate containers, respectively.

EXAMPLE 2

The saccharifying enzyme is contained in one ore more water-soluble small bags, and the bags are mixed with the cyclodextrin clathrate compound and are kept together in a container.

EXAMPLE 3

Each dose of saccharifying enzyme is contained in a water-soluble small bag, and a dose of cyclodextrin clathrate compound is contained in a water-soluble container together with the water-soluble small container.

EXAMPLE 4

A partition is formed in a water-soluble container to form two spaces, in one of which the cyclodextrin clathrate compound is contained and in the other of which the saccharifying enzyme is contained.

When the saccharifying enzyme thus prepared is poured into the bath, the temperature of which is about 40° C. and is suitable for the activities of the saccharifying enzyme, the saccharifying enzyme acts on the rings of the cyclodextrin clathrate compound contained in the bath preparations to open the rings. As a result, the component of milk, which has been included in the cyclodextrin clathrate compound, is dissociated and dissolved in the bath water, and the bath preparations of the present invention have effects for refreshing the skin.

EMBODIMENT 1

(Powder Type)

Thirty-five parts by weight of sodium sulfate; 45 parts by weight of sodium hydrogencarbonate; 20 parts of cyclodextrin clathrate compound of a component of milk; and a small amount of perfumes (milk flavor) were mixed and agitated in a kneader, and a powder type bath preparation was obtained.

EMBODIMENT 2

(Powder Type)

Forty-two parts by weight of sodium sulfate; 46 parts by weight of sodium hydrogencarbonate; 10 parts of cyclodextrin clathrate compound of a component of milk produced from the reduced cyclodextrin syrup (vitamins and egg white were added after inclusion process); 2 parts of borax; a small amount of perfume (jasmin); and a small amount of uranine were mixed and agitated in a kneader, and powder type bath preparation was obtained.

EMBODIMENT 3

(Powder Type)

Forty-six parts by weight of sodium sesquicarbonate; 12 parts by weight of sodium chloride; 40 parts of cyclodextrin clathrate compound of a component of milk (vitamins and egg white were added after inclusion process); 2 parts of medicial herbs; a small amount of perfumes (jasmin); and a small amount of uranine were mixed and agitated in a kneader, and a powder type bath preparation was obtained.

EMBODIMENT 4

(Granule Type)

Thirty-five parts by weight of sodium sulfate; 44 parts by weight of sodium hydrogencarbonate; 20 parts of cyclodextrin clathrate compound of a component of milk (vitamins and perfumes were added after inclusion process); and 1 part by weight of carboxymethylcellulose were mixed and agitated in a kneader. The mixture was pressed to form blocks, and the blocks were crushed and filtered to form a granule type bath preparation.

EMBODIMENT 5

(Tablet Type)

Thirty-five parts by weight of sodium sesquicarbonate; 8 parts by weight of sodium chloride; 32 parts of cyclodextrin clathrate compound of a component of milk (vitamins, egg white and perfumes were added after inclusion process); 25 parts of borax; and a small amount of uranine were mixed and agitated in a kneader, and the mixed powder was compression molded by means of a tablet machine to form a tablet type bath preparation.

EMBODIMENT 6

(Powder Type)

Thirty-two parts by weight of sodium sulfate; 44 parts by weight of sodium carbonate; 23 parts of cyclodextrin clathrate compound of a component of milk (vitamins and perfumes were added after inclusion process); a small amount of uranine; and a small amount of saccharifying enzyme were mixed and agitated in a kneader, and a powder type bath preparation was obtained.

ADVANTAGES OF THE INVENTION

The bath preparations of the present invention comprise a cyclodextrin clathrate compound of a component of milk, and accordingly, the bath preparations of the present invention can achieve effects for refreshing the skin.

According to the present invention, a component of milk, such as a component of cow's milk, is included in the cyclodextrin and is very stable and is durable against degradation. Accordingly, the industrial production and administration of bath preparations of the present invention is very easy.

Further, it is easy to add vitamins and perfumes to the cyclodextrin clathrate compound of a component of milk of the present invention. The cyclodextrin clathrate compound of the present invention is readily powdered. Accordingly, it is easy to produce bath preparations from the cyclodextrin clathrate compound of a component of milk.

In addition, when the bath preparations of the present invention are used with saccharifying enzyme, the cyclodextrin clathrate compound can be readily dissociated, and the component of milk included in the cyclodextrin clathrate compound functions effectively.

When the end-groups of maltooligosaccharide syrup are almost completely reduced, and then, reduced cyclodextrin syrup, which is a mixture of the reduced syrup and cyclodextrin, is used to include a component of milk to form cyclodextrin clathrate compound of a component of milk, the reduced cyclodextrin syrup has a more uniform dispersion capability of the cyclodextrin and the inclusion capability is increased.

When a commercial cyclodextrin containing malt syrup is used to produce a cyclodextrin clathrate compound of a component of milk, the scorching, i.e., oxidation, of syrup may occur if the treating temperature is high. As a result, there may occur a problem that the component of milk cannot be fully included in cyclodextrin. In such a case, it is preferred that end-groups of maltooligosaccharide syrup are substantially completely reduced, and that then, the reduced cyclodextrin syrup, which is a mixture of the reduced syrup and cyclodextrin, is used to include the component of milk to form cyclodextrin clathrate compound of the component of milk. Therefore, the syrup will not be easily oxidized, and its stability against high temperature is increased. Further, the syrup will not be easily colored, since the reaction with amino groups, such as amino acid, i.e., amino carbonyl reaction, does not occur.

When a cyclodextrin containing syrup is used to include a component of milk therein, the obtained cyclodextrin clathrate compound is not dissociated, i.e., its rings are not open, until it is heated to a relatively temperature, for example, between 80° and 130° C. under the dry conditions. Contrary to this, when the reduced cyclodextrin syrup is used to include a component of milk therein, the produced cyclodextrin clathrate compound can be dissociated easily, and the cyclodextrin clathrate compound can be readily dispersed in water.

It is preferred that the perfumes, which are mixed with the cyclodextrin clathrate compound of a component of milk, are included in the reduced cyclodextrin syrup, because thus obtained cyclodextrin clathrate compound of the perfumes is preferable for bath preparations since it is stable and since it can be readily dispersed in water or warm water and dissolved therein.

What is claimed is:

1. A stable Bath preparation comprising a cyclodextrin clathrate compound of a component of milk.

2. A stable bath preparation according to claim 1, further comprising egg white.

3. A stable bath preparation according to claim 1, further comprising at least one vitamin.

4. A stable bath preparation according to claim 3, wherein said at least one vitamin is selected from the group consisting of vitamin A, vitamins B, vitamin C, Vitamin D, vitamin E, vitamin F and vitamin P.

5. A stable bath preparation according to claim 3, wherein said bath preparation further comprises a saccharifying enzyme.

6. A stable bath preparation according to claim 5, wherein said saccharifying enzyme and said cyclodextrin clathrate compound are mixed.

7. A stable bath preparation according to claim 5, wherein said saccharifying enzyme is isolated from said cyclodextrin clathrate compound.

8. A stable bath preparation according to claim 1, wherein said bath preparation further comprises a saccharifying enzyme.

9. A stable bath preparation according to claim 8, wherein said saccharifying enzyme and said cyclodextrin clathrate compound are mixed.

10. A stable bath preparation according to claim 8, wherein said saccharifying enzyme is isolated from said cyclodextrin clathrate compound.

11. A method for producing a bath preparation which comprises:
   substantially reducing the number of reducing end-groups of a maltooligosaccharide syrup containing cyclodextrin to form a reduced syrup;
   contacting milk with the reduced syrup containing cyclodextrin to form a cyclodextrin clathrate compound of a component of milk;
   mixing said cyclodextrin clathrate compound of said component of milk with conventional bath materials.

12. A method for producing a bath preparation according to claim 11, wherein said milk is selected from the group consisting of cow's milk, components of cow's milk, powdered milk, evaporated milk, components of evaporated milk, raw cream and components of raw cream.

13. A method for producing a bath preparation according to claim 12, wherein said number of reducing end-groups of said maltooligosaccharide syrup containing cyclodextrin is hydrogenated under nickel catalyst and high pressure so as to reduce said number of reducing end-groups of said maltooligosaccharide syrup.

14. A method for producing a bath preparation according to claim 12, which comprises:
   adding egg white to said milk;
   contacting said milk with said reduced syrup containing cyclodextrin to form said cyclodextrin clathrate compound of said component of milk;
   drying said cyclodextrin clathrate compound of said component of milk to form a powder cyclodextrin clathrate compound; and
   mixing said powder cyclodextrin clathrate compound of said component of milk with conventional bath materials and at least one vitamin.

15. A method for producing a bath preparation according to claim 12, which comprises:
   contacting said milk with said reduced syrup containing cyclodextrin to form said cyclodextrin clathrate compound of said component of milk;
   drying said cyclodextrin clathrate compound of said component of milk to form a powder cyclodextrin clathrate compound; and
   mixing said powder cyclodextrin clathrate compound of said component of milk with conventional both materials and at least one vitamin.

16. A method for producing a bath preparation according to claim 12, which comprises:
   contacting said milk with said reduced syrup containing cyclodextrin to form said cyclodextrin clathrate compound of said component of milk;
   mixing at least one vitamin with liquid material containing said cyclodextrin clathrate compound of said component of milk;
   drying the mixture of said at least one vitamin and said cyclodextrin clathrate compound of said component of milk at a relatively low temperature to form a powder cyclodextrin clathrate compound; and
   mixing said powder cyclodextrin clathrate compound with conventional bath materials.

17. A method for producing a bath preparation according to claim 12, which comprises:
   contacting said milk with said reduced syrup containing cyclodextrin to form said cyclodextrin clathrate compound of said component of milk;
   drying said cyclodextrin clathrate compound of said component of milk to form a powder cyclodextrin clathrate compound; and
   mixing said powder cyclodextrin clathrate compound of said component of milk with a saccharifying enzyme and conventional bath materials.

18. A method for producing a bath preparation which comprises:
   substantially reducing the number of reducing end-groups of a maltooligosaccharide syrup containing cyclodextrin to form a reduced syrup;
   adding additional cyclodextrin to the reduced syrup;
   contacting milk with the reduced syrup containing cyclodextrin to form a cyclodextrin clathrate compound of a component of milk;
   mixing said cyclodextrin clathrate compound of said component of milk with conventional bath materials.

19. A method for producing a bath preparation according to claim 18, which comprises:
   adding egg white to said milk;

contacting said milk with said reduced syrup containing cyclodextrin to form said cyclodextrin clathrate compound of said component of milk;

drying said cyclodextrin clathrate compound of said component of milk to form a powder cyclodextrin clathrate compound; and mixing said powder cyclodextrin clathrate compound of said component of milk with conventional bath materials and at least one vitamin.

20. A method for producing a bath preparation according to claim 18, which comprises:

contacting said milk with said reduced syrup containing cyclodextrin to form said cyclodextrin clathrate compound of said component of milk;

mixing at least one vitamin with liquid material containing said cyclodextrin clathrate compound of said component of milk;

drying the mixture of said at least one vitamin and said cyclodextrin clathrate compound of said component of milk at a relatively low temperature to form a powder cyclodextrin clathrate compound; and mixing said powder cyclodextrin clathrate compound with conventional bath materials.

21. A method for producing a bath preparation according to claim 18, which comprises:

contacting said milk with said reduced syrup containing cyclodextrin to form said cyclodextrin clathrate compound of said component of milk;

drying said cyclodextrin clathrate compound of said component of milk to form a powder cyclodextrin clathrate compound; and mixing said powder cyclodextrin clathrate compound of said component of milk with a saccharifying enzyme and conventional bath materials.

* * * * *